United States Patent [19]

Corteel

[11] 4,387,005

[45] Jun. 7, 1983

[54] PROCESS AND APPARATUS FOR CARRYING OUT THE FIRST STAGE OF SEPARATION OF CONSTITUENTS OF A REACTION MIXTURE OBTAINED DURING SYNTHESIS OF ASYMMETRIC DIMETHYLHYDRAZINE BY THE RASCHIG METHOD

[75] Inventor: Guy Corteel, Gaillon, France

[73] Assignee: Societe Europeenne de Propulsion, Puteaux, France

[21] Appl. No.: 269,574

[22] Filed: Jun. 2, 1981

[30] Foreign Application Priority Data

Jun. 4, 1980 [FR] France ............................... 80 12441

[51] Int. Cl.³ .............................................. B01D 3/14
[52] U.S. Cl. ...................................... 203/81; 203/99; 564/499
[58] Field of Search .............. 564/497, 499, 310, 314; 203/71, 81, 86, 99, 100

[56] References Cited

U.S. PATENT DOCUMENTS 3,098,017 7/1963 Walter et al. ......................... 203/59

Primary Examiner—Frank Sever
Attorney, Agent, or Firm—Weingarten, Schurgin, Gagnebin & Hayes

[57] ABSTRACT

The present invention relates to a process for carrying out the first stage of separation of constituents of a reaction mixture obtained during synthesis of asymmetric dimethylhydrazine by the Raschig method, consisting in sending, into an empty central section (B) of a column, the reaction mixture coming from said synthesis, this central section being surmounted by a column (C) in which is effected separation of the volatile compounds contained in said mixture and being extended downwardly by an exhausting section (A).

5 Claims, 1 Drawing Figure

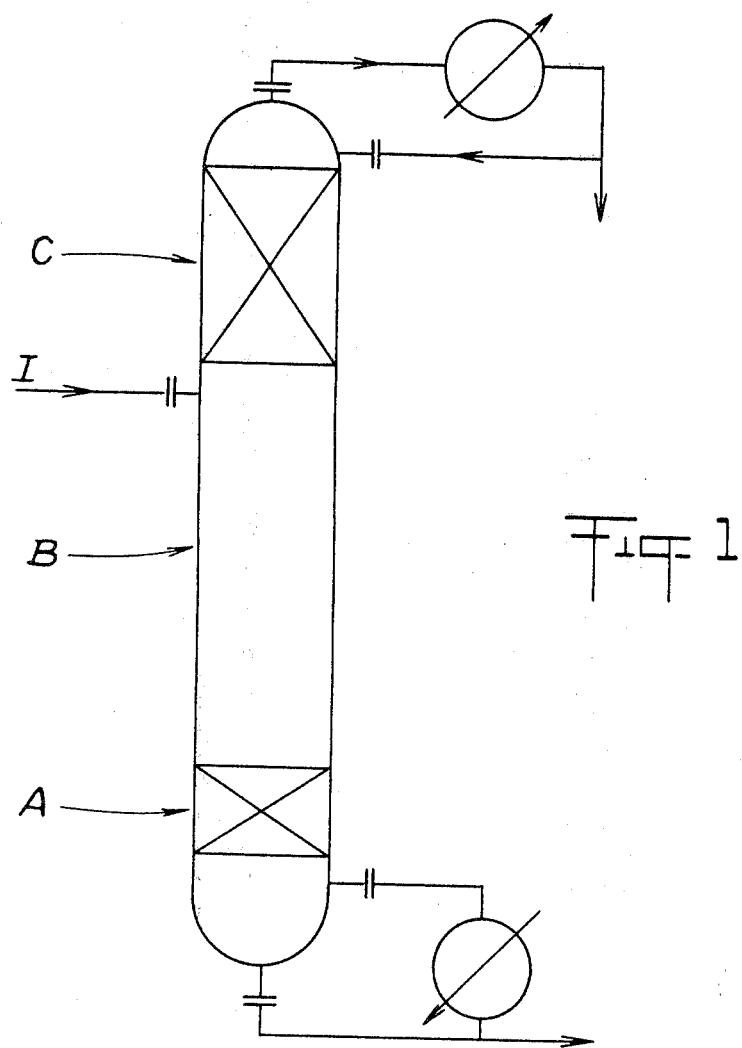

PROCESS AND APPARATUS FOR CARRYING OUT THE FIRST STAGE OF SEPARATION OF CONSTITUENTS OF A REACTION MIXTURE OBTAINED DURING SYNTHESIS OF ASYMMETRIC DIMETHYLHYDRAZINE BY THE RASCHIG METHOD

The present invention relates to a process and apparatus for carrying out the first stage of separation of constituents of a reaction mixture obtained during synthesis of asymmetric dimethylhydrazine by the Raschig method.

The solution obtained by the Raschig method for producing asymmetric dimethylhydrazine comprises, according to the conditions of operation, for 1 kg of solution, about:

1 to 2 moles of ammonia
2 to 8 moles of dimethylamine
0.01 to 0.1 mole of formaldehyde dimethylhydrazone
0.4 to 0.8 mole of asymmetric dimethylhydrazine
1 to 3 moles of sodium chloride
0.2 to 0.8 mole of sodium hydroxide and water.

It is from this solution that an asymmetric dimethylhydrazine having precise technical specifications can be recovered.

According to a known technique, the first stage of this recovery consists in subjecting the solution to an operation of distillation with a view to separating on the one hand the "volatile compounds" (which are by definition dimethylamine, ammonia and formaldehyde dimethylhydrazone) and on the other hand the "non-volatile" compounds (which are by definition asymmetric dimethylhydrazine, sodium chloride, sodium hydroxide and water).

When, to carry out this first stage of recovery, a conventional distilling column is used, supply of said column must be effected in a zone where, at equilibrium, the concentration of "volatile compounds" (particularly dimethylamine) is considerable, this sometimes involving a precipitation of the sodium chloride (which is often in the starting solution at the limit of saturation) and clogging of the column.

To overcome this difficulty, a technique has already been recommended, consisting in carrying out, in an apparatus of the evaporator type, a first, rough separation of the starting solution so as to obtain a gaseous phase and a liquid phase then in introducing in a single distilling column on the one hand, towards the top of the column, said gaseous phase and, on the other hand, towards the bottom of the column, said liquid phase. Taking into account the voluntarily very rough character of the first separation, the gaseous phase contains considerable quantities of "non-volatile" compounds, with the result that the distilling column must comprise, between the intake points of the gaseous phase and of the liquid phase, a large number of plates. The process is designed so that the maximum concentration of the least volatile organic compound occurs in the distilling column between the intake points of the gaseous phase and of the liquid phase.

The solution described hereinabove is technically valid but has the drawback of being relatively expensive from the standpoint of investment.

It has been possible, according to the present invention, to overcome the difficulties mentioned above by using a distilling apparatus of this type provided that it is constituted by three sections;

an empty central section (B), forming clearance volume and receiving the feed fluid,
an upper section (C) solely carrying out rectified distillation of the "volatile compounds" contained in the feed mixture
a lower section (A) in which said volatile compounds are exhausted.

The starting mixture may be fed either at the base or towards the top of this clearance volume.

When feed is effected at the base of the clearance volume, the column functions exactly like the juxtaposition of two columns. When feed is effected towards the top of the clearance volume, it is advantageous to introduce the solution in the form of a film or droplets so as to carry out certain exchanges between this solution and the vapours present in the clearance volume.

In all cases, the low part (A) of the distilling column will have 2 to 3 theoretical plates and a reflux ratio of 3 to 7, the top part (C) of the distilling column will advantageously have 7 to 10 theoretical plates.

The apparatus according to the invention is schematically shown in FIG. 1.

In this FIGURE it is observed that the distilling column is composed of three sections referenced A, B and C. Solution is fed into section B at any point between the top of section A and the base of section B. When feed is effected at a certain height above the top of section A, it is desirable to provide a large exchange surface between the rising vapour of section A and said solution; to this end, the falling film or spray technique may be used for the solution.

Section B does not comprise any internal distilling elements (packing or plates). It may have any diameter, equal to or different from the diameter of elements A and C.

The section B has the following functions:
possible pre-evaporation of the feed,
creation of a buffer clearance volume for absorbing a possible drift of functioning of the conventional distillation sections A and C; in the hypothesis of an accidental accumulation of organic constituents in the apparatus, these constituents may find a place in the section B, without risking an undesirable precipitation of the sodium chloride.

The present invention includes a process for carrying out the first stage of separation of constituents of a reaction mixture obtained during synthesis of asymmetric dimethylhydrazine by the Raschig method, comprising the following steps. First, subject to reaction mixture to a distillation at a low reflux ratio, just sufficient to take along in gaseous form only the volatile parts of the mixture accompanied by small quantities of water and asymmetric dimethylhydrazine. Second, subject the gaseous phase to a second distillation so as to separate, in liquid form, the small quantities of water and asymmetric dimethylhydrazine carried in the gaseous phase.

The following example illustrates the invention.

EXAMPLE 1

It is desired to separate a mixture containing, for 1 kg of mixture, 1.27 mole of ammonia, 4.38 moles of dimethylamine, 0.026 mole of formaldehyde dimethylhydrazone, 0.56 mole of asymmetric dimethylhydrazine, 33.9 moles of water, 2 moles of sodium chloride, 0.45 mole of sodium hydroxide.

The apparatus is designed so that it comprises:
two equivalent plates in section A,
seven equivalent plates in section C, and a clearance volume B extending over about half the total height of the column.

The reflux ratio being 7, the apparatus makes it possible to recover all the ammonia and dimethylamine, 88% of the formaldehyde dimethylhydrazone at the top, and 99% of the dimethylhydrazine at the bottom without precipitation of salt.

What is claimed is:

1. A method of separating a feed fluid into constituents according to a reaction process comprising the steps of:

providing a distilling apparatus comprising an empty central section forming a clearance volume and receiving said feed fluid, an upper section for providing rectified distillation of volitile compounds contained in said feed fluid, and a lower section into which volitile compounds are exhausted; feeding said feed fluid into said clearance volume; and withdrawing said volitile compounds from said lower section.

2. The method of claim 1, further including the step of providing a large exchange surface between said feed mixture and said vapor of said lower section.

3. The method of claim 1 wherein said reaction process comprises the Raschig method.

4. The method of claim 3 further including the step of subjecting the reaction mixture within said distilling apparatus to a first distillation at a reflux ratio between 3 and 7 inclusive, wherein a gaseous phase is produced.

5. The method of claim 4 used to synthesize asymmetric dimethylhydrazine, further comprising the step of subjecting said gaseous phase to a second distillation to separate, in liquid form, water and asymmetric dimethylhydrazine.

* * * * *